United States Patent
Yakami et al.

(10) Patent No.: US 9,734,299 B2
(45) Date of Patent: Aug. 15, 2017

(54) DIAGNOSIS SUPPORT SYSTEM, METHOD OF CONTROLLING THE SAME, AND STORAGE MEDIUM

(71) Applicant: CANON KABUSHIKI KAISHA, Tokyo (JP)

(72) Inventors: Masahiro Yakami, Kyoto (JP); Koji Fujimoto, Kyoto (JP); Masami Kawagishi, Kyoto (JP); Gakuto Aoyama, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 231 days.

(21) Appl. No.: 14/311,392

(22) Filed: Jun. 23, 2014

(65) Prior Publication Data

US 2015/0019473 A1 Jan. 15, 2015

(30) Foreign Application Priority Data

Jul. 10, 2013 (JP) ................. 2013-144857

(51) Int. Cl.
G06F 9/44 (2006.01)
G06N 7/02 (2006.01)
G06N 7/06 (2006.01)
G06F 19/00 (2011.01)

(52) U.S. Cl.
CPC ................. *G06F 19/345* (2013.01)

(58) Field of Classification Search
USPC ......................................... 706/52
See application file for complete search history.

(56) References Cited

U.S. PATENT DOCUMENTS

| | | | | |
|---|---|---|---|---|
| 8,880,455 B2* | 11/2014 | Kawagishi | ............ | G06F 19/321 706/45 |
| 8,949,171 B2* | 2/2015 | Kawagishi | ............ | G06F 19/321 706/52 |
| 9,117,009 B2* | 8/2015 | Iizuka | ................... | G06F 19/321 |
| 9,361,580 B2* | 6/2016 | Kawagishi | ............... | G06N 5/02 |
| 9,384,326 B2* | 7/2016 | Kawagishi | ............. | G06F 19/345 |
| 9,436,915 B2* | 9/2016 | Kawagishi | ............ | G06F 19/321 |

(Continued)

FOREIGN PATENT DOCUMENTS

| | | |
|---|---|---|
| JP | 2010-200840 A | 9/2010 |
| JP | 2011-131022 A | 7/2011 |
| JP | 2012-115446 A | 6/2012 |

OTHER PUBLICATIONS

A Universal Fault Diagnostic Expert System Based on Bayesian Network Ting Han; Bo Li; Limei Xu 2008 International Conference on Computer Science and Software Engineering Year: 2008, vol. 1 pp. 260-263, DOI: 10.1109/CSSE.2008.946 IEEE Conference Publications.*

(Continued)

*Primary Examiner* — Michael B Holmes
(74) *Attorney, Agent, or Firm* — Carter, DeLuca, Farrell & Schmidt, LLP

(57) ABSTRACT

A diagnosis support system obtains input information corresponding to a case, identifies a diagnosis corresponding to the case based on the input information, obtains the inference probability of the diagnosis, and displays supporting information corresponding to the inference probability of the identified diagnosis on a display unit.

20 Claims, 5 Drawing Sheets

(56) References Cited

U.S. PATENT DOCUMENTS 9,519,866 B2 * 12/2016 Kawagishi .......... G06F 19/3443

OTHER PUBLICATIONS

Sensitivity analysis of multi-attribute decision making methods in Clinical Group Decision Support System Sri Kusumadewi; Sri Hartati 2007 International Conference on Intelligent and Advanced Systems Year: 2007 pp. 301-304, DOI: 10.1109/ICIAS.2007.4658395 IEEE Conference Publications.*

Generalized fuzzy certainty factor and fuzzy decision set: An application to surgery intelligence Adala Sadana; P. Venkata Subba Reddy 2015 International Conference on Fuzzy Theory and Its Applications (iFUZZY) Year: 2015 pp. 121-126, DOI: 10.1109/iFUZZY.2015.7391905 IEEE Conference Publications.*

Gearbox fault diagnosis using vibration and current information fusion Yayu Peng; Wei Qiao; Liyan Qu; Jun Wang 2016 IEEE Energy Conversion Congress and Exposition (ECCE) Year: 2016 pp. 1-6, DOI: 10.1109/ECCE.2016.7855132 IEEE Conference Publications.*

Information granules in medical differential diagnosis Shusaku Tsumoto; Shoji Hirano 2012 IEEE International Conference on Systems, Man, and Cybernetics (SMC) Year: 2012 pp. 395-401, DOI: 10.1109/ICSMC.2012.6377733 IEEE Conference Publications.*

Decision support by fusion in endoscopic diagnosis M. M. Zheng; S. M. Krishnan The Seventh Australian and New Zealand Intelligent Information Systems Conference, 2001 Year: 2001 pp. 107-110, DOI: 10.1109/ANZIIS.2001.974059 IEEE Conference Publications.*

Japanese office action issued in corresponding application No. 2013144857 dated May 12, 2017.

* cited by examiner

FIG. 4

| j | $I_j$ (IMAGE FINDING NAME OR CLINICAL INFORMATION NAME) | jk | $S_{jk}$ (STATE NAME) |
|---|---|---|---|
| 1 | SHAPE | 11 | SPHERICAL |
| | | 12 | LOBULATED |
| | | 13 | RAGGED |
| 2 | NOTCH | 21 | STRONG |
| | | 22 | INTERMEDIATE |
| | | 23 | WEAK |
| | | 24 | NONE |
| 3 | FINE SPICULATION | 31 | STRONG |
| | | 32 | INTERMEDIATE |
| | | 33 | WEAK |
| | | 34 | NONE |
| 4 | AIR BRONCHOGRAM | 41 | PRESENT |
| | | 42 | SUSPICIOUS |
| | | 43 | NONE |
| ... | | | |
| l | INVOLVEMENT(BRONCHUS) | l1 | PRESENT |
| | | l2 | SUSPICIOUS |
| | | l3 | NONE |
| ... | | | |
| m | HISTORY OF MALIGNANCY | m1 | PRESENT |
| | | m2 | NONE |

FIG. 5A

| $E_x$ | $I(D_1|E_x)$ [%] | $I(D_2|E_x)$ [%] | $I(D_3|E_x)$ [%] |
|---|---|---|---|
| {$S_{12}$} | 10.4 | -7.21 | -3.19 |
| {$S_{21}$} | 7.13 | -9.16 | 2.03 |
| {$S_{33}$} | -2.16 | 4.23 | -2.07 |
| {$S_{43}$} | 2.51 | 5.29 | -8.80 |
| {$S_{l1}$} | 4.09 | 1.01 | -5.10 |
| {$S_{m2}$} | 8.23 | -13.8 | 5.57 |

| $P(D_1|E)$ [%] | $P(D_2|E)$ [%] | $P(D_3|E)$ [%] |
|---|---|---|
| 47.6 | 25.1 | 28.3 |

FIG. 5B

| $E_x$ | $I(D_1|E_x)$ [%] | $I(D_2|E_x)$ [%] | $I(D_3|E_x)$ [%] |
|---|---|---|---|
| {$S_{11}$} | -7.25 | 10.4 | -3.15 |
| {$S_{24}$} | -6.23 | 8.41 | -2.18 |
| {$S_{34}$} | -7.15 | 8.61 | -1.46 |
| {$S_{43}$} | 2.51 | 5.29 | -8.80 |
| {$S_{l3}$} | -5.24 | 3.96 | 1.28 |
| {$S_{m1}$} | -10.8 | 9.76 | 1.04 |

| $P(D_1|E)$ [%] | $P(D_2|E)$ [%] | $P(D_3|E)$ [%] |
|---|---|---|
| 6.08 | 82.1 | 11.8 |

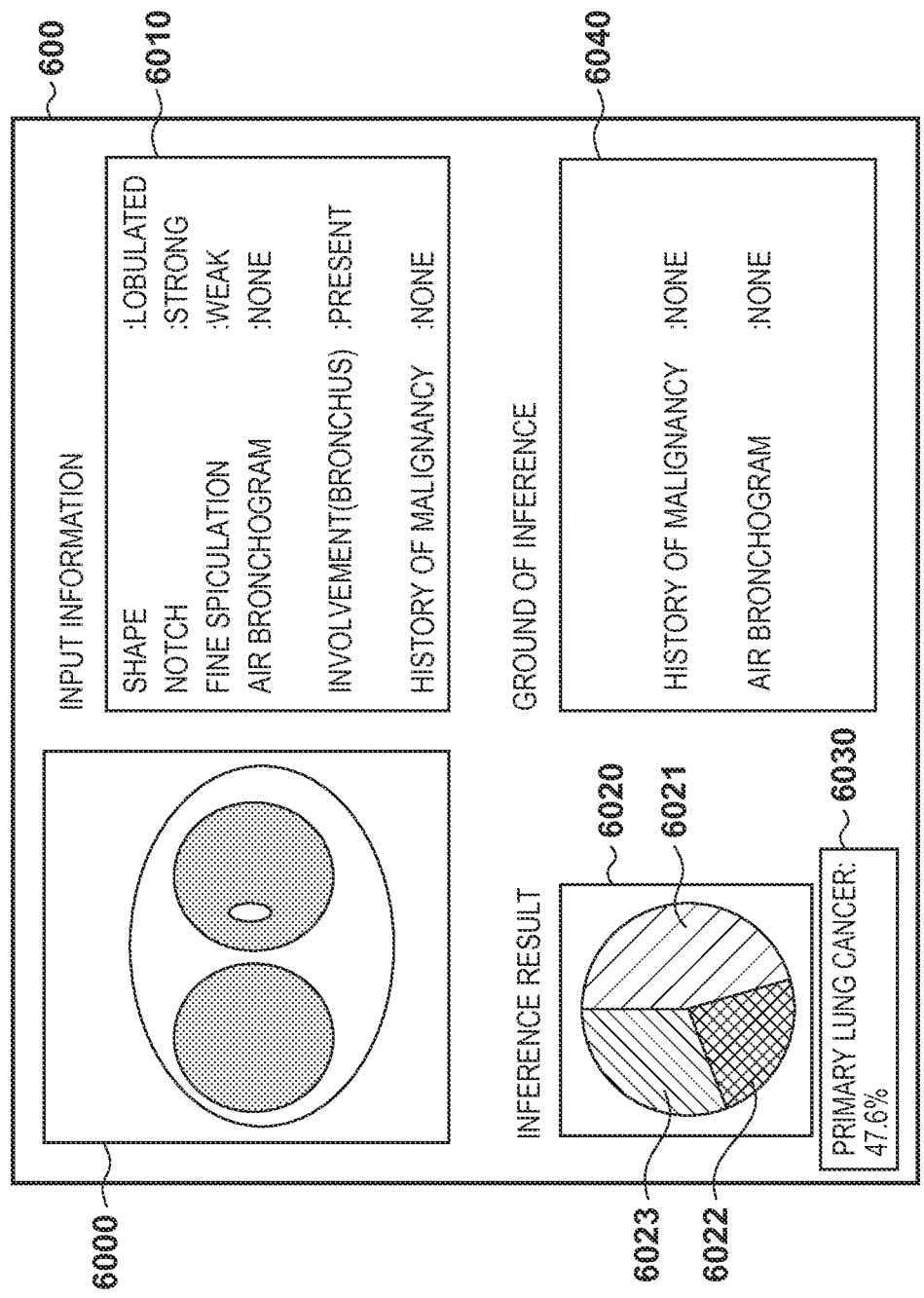

DIAGNOSIS SUPPORT SYSTEM, METHOD OF CONTROLLING THE SAME, AND STORAGE MEDIUM

BACKGROUND OF THE INVENTION

Field of the Invention

The present invention relates to a diagnosis support system and, more particularly, to a diagnosis support system which provides information for supporting medical diagnosis.

Description of the Related Art

In the medical field, doctors perform image diagnosis in which diagnosis is performed by interpreting the medical images obtained by imaging apparatuses such as an X-ray CT apparatus and an MRI. When, for example, performing image diagnosis, a doctor identifies the symptom of a lesion depicted in an image by comprehensively determining the findings (to be referred to as "image findings" hereinafter) obtained from images and various types of measurement values in accordance with a radiogram interpretation request from a primary doctor. The doctor then compiles the process of reaching the image diagnosis into a radiogram interpretation report to the primary doctor as the request source by using image findings and measurement values.

For the purpose of reducing the load of radiogram interpretation on a doctor, there has been developed a medical diagnosis support apparatus (to be referred to as a "decision support apparatus" hereinafter) which supports diagnosis by detecting an abnormal shadow or the like in a medical image and inferring the state of the shadow by computer processing. In general, when using such a decision support apparatus, first of all, the doctor performs radiogram interpretation. The doctor then refers to the supporting information provided by the decision support apparatus and compares it with the result of the radiogram interpretation made by himself/herself, thereby making final determination. In order to rely on the supporting information presented by the decision support apparatus, it is preferable that the doctor knows the specific ground on which this supporting information is derived. That is, the decision support apparatus preferably presents the ground of an inference concerning supporting information to be presented.

Under the circumstances, a decision support apparatus for presenting such grounds of inferences has been developed. For example, Japanese Patent Laid-Open No. 2010-200840 proposed by the present applicants discloses a technique of presenting denial information and affirmative information as support information with respect to the inference result obtained by an apparatus based on already input information such as image findings. Japanese Patent Laid-Open No. 2010-200840 discloses a technique of presenting denial information and affirmative information concerning each possible diagnosis as supporting information. This allows the decision support apparatus to present an inference result, and can present, as supporting information, information influencing the derivation of the inference result from the apparatus based on information such as image findings.

When performing radiogram interpretation, doctors tend to use, as key information, information affirming an estimated diagnosis when he/she is confident of the estimated diagnosis, and information denying other diagnoses when he/she is not confident of the estimated diagnosis. However, the technique disclosed in Japanese Patent Laid-Open No. 2010-200840 has a problem that such information cannot be sometimes presented as supporting information.

SUMMARY OF THE INVENTION

The present invention provides a technique capable of efficiently presenting information necessary to improve the certainty factor of diagnosis by a doctor.

According to one aspect of the present invention, there is provided a diagnosis support system comprising: an obtaining unit configured to obtain input information corresponding to a case; an inference unit configured to identify a diagnosis corresponding to the case based on the input information and obtain an inference probability of the diagnosis; and a display control unit configured to display supporting information corresponding to the inference probability of the identified diagnosis on a display unit.

Further features of the present invention will become apparent from the following description of exemplary embodiments (with reference to the attached drawings).

BRIEF DESCRIPTION OF THE DRAWINGS

FIG. 4 is a view showing an example of image findings and clinical information in the first embodiment;

FIGS. 5A and 5B are views each showing an example of influence degrees in the first embodiment; and FIG. 6 is a view showing an example of supporting information in the first embodiment.

DESCRIPTION OF THE EMBODIMENTS

A mode (embodiment) for carrying out the present invention will be described below with reference to the accompanying drawings. However, the scope of the present invention is not limited to the illustrated examples.

First Embodiment

A diagnosis support system according to the first embodiment obtains medical information concerning a case as a medical diagnosis target and performs diagnosis support for the case. Assume that in this embodiment, the diagnosis support system obtains a plurality of image findings, a past medical history, and a tumor marker value (to be referred to as medical information hereinafter) concerning an abnormal shadow in a lung as medical information. This diagnosis support system performs inference about the abnormality type (diagnosis) of the abnormal shadow in the lung based on the obtained information. The diagnosis support system then presents diagnosis supporting information based on the inference result. The above case will be described as an example. Note that an inference target is not limited to this, and diagnoses, image findings which can be input, clinical information, and the like which will be described below each are merely an example for explaining a processing procedure in the diagnosis support system.

Figure 1:
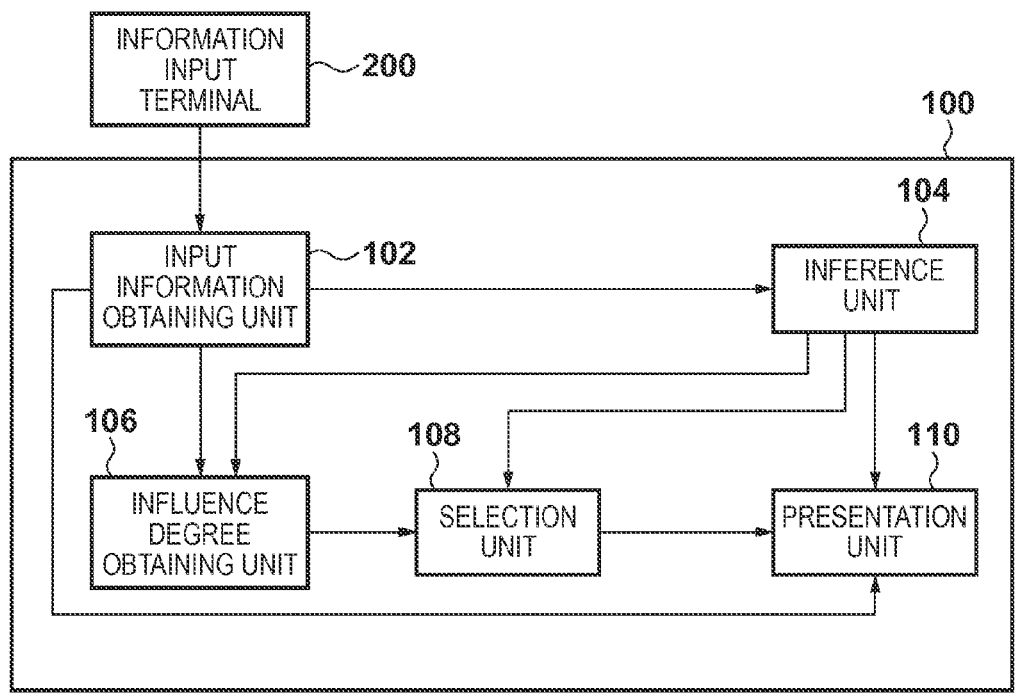
FIG. 1 is a block diagram showing the device configuration of a decision support apparatus according to the first embodiment.

FIG. 1 shows the arrangement of a decision support apparatus in the system according to the first embodiment.

A decision support apparatus 100 according to this embodiment includes an input information obtaining unit 102, an inference unit 104, an influence degree obtaining unit 106, a selection unit 108, and a presentation unit 110. The decision support apparatus 100 is connected to an information input terminal 200.

The information input terminal 200 obtains case information (electronic medical chart information including medical images and clinical information) concerning an abnormal shadow in a lung which corresponds to a case as a diagnosis target from a server (not shown) according to operation by the user (doctor). Note that the information input terminal 200 may be connected to external storage devices, for example, an FDD, HDD, CD drive, DVD drive, MO drive, and ZIP drive to obtain case information from these drives. The information input terminal 200 displays these pieces of case information in a form that allows radiogram interpretation.

The user inputs image findings corresponding to the case information displayed on a monitor as a display unit by using a mouse and a keyboard. This processing can be implemented by making the information input terminal 200 have a function which can be selected with a GUI using, for example, a template type input support method. Assume that in this embodiment, image findings and clinical information respectively include a name and a state, as will be described later. In addition, the user may input image findings with the information input terminal by referring to the display on the monitor, while clinical information may be automatically input to a template or input by the user. The information input terminal 200 transmits image findings and clinical information, together with accompanying data (representative image or the like), to the decision support apparatus 100 via a LAN or the like in accordance with the operation performed by the user.

The input information obtaining unit 102 obtains information (to be referred to as input information hereinafter) concerning an abnormal shadow in a lung which is input from the information input terminal 200 to the decision support apparatus 100 and accompanying data (to be collectively referred to, together with input information, as medical information hereinafter), and outputs these pieces of information to the inference unit 104, the influence degree obtaining unit 106, and the presentation unit 110. The inference unit 104 executes inference processing concerning an abnormal shadow in a lung as a diagnosis target based on the input information obtained by the input information obtaining unit 102, and calculates the probability (inference result) of the abnormal shadow being each diagnosis. The calculated inference result is output to the influence degree obtaining unit 106, the selection unit 108, and the presentation unit 110. Inference processing will be described later.

The influence degree obtaining unit 106 obtains an influence degree by using the input information obtained by the input information obtaining unit 102 and the inference result obtained by the inference unit 104, and outputs the obtained influence degree to the selection unit 108. A method of obtaining an influence degree will be described later. The selection unit 108 selects information based on the inference result obtained by the inference unit 104 and the influence degree obtained by the influence degree obtaining unit 106. The information selected by the selection unit 108 is output to the presentation unit 110. The presentation unit 110 generates and displays information to be presented. More specifically, the presentation unit 110 generates information to be presented based on the input information and accompanying data obtained by the input information obtaining unit 102, the inference result obtained by the inference unit 104, and the information selected by the selection unit 108, and performs display control of the generated information.

Note that at least some of the units of the decision support apparatus 100 shown in FIG. 1 may be implemented as independent devices. Alternatively, each unit may be implemented as software which implements the corresponding function. Assume that in this embodiment, each unit is implemented by software.

Figure 2:
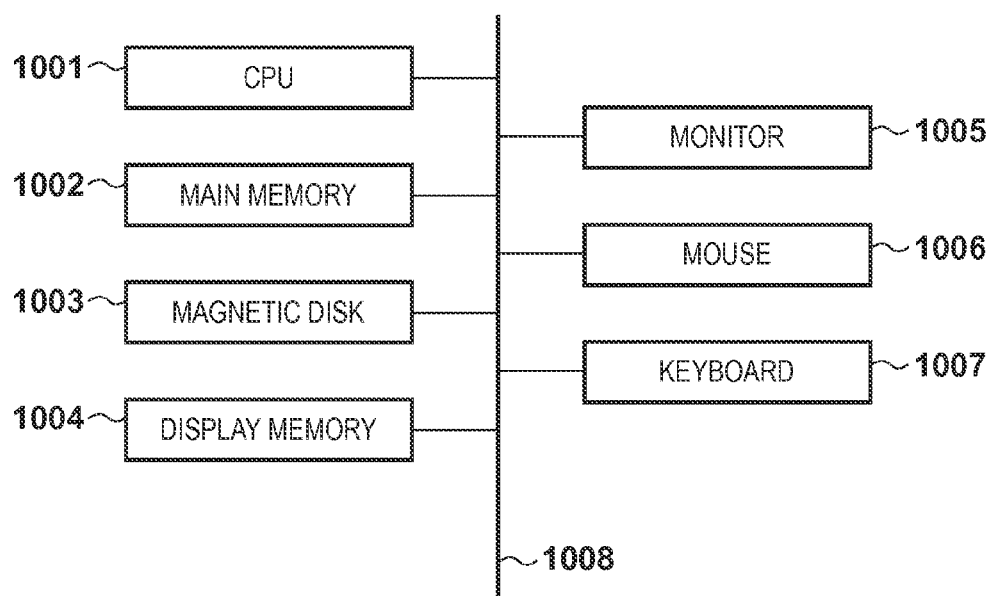
FIG. 2 is a block diagram showing the basic arrangement of a computer which implements each unit of the decision support apparatus by software.

FIG. 2 is a block diagram showing the basic arrangement of a computer for implementing the function of each unit shown in FIG. 1 by executing software. A CPU 1001 mainly controls the operation of each constituent element. A main memory 1002 stores a control program executed by the CPU 1001 and provides a work area at the time of execution of a program by the CPU 1001. A magnetic disk 1003 stores an operating system (OS), device drives for peripheral devices, various types of application software including programs for performing processing and the like (to be described later), and the like. A display memory 1004 temporarily stores display data. A monitor 1005 is, for example, a CRT monitor or a liquid crystal monitor, and displays images, texts, and the like based on data from the display memory 1004. The user performs pointing input and inputs characters and the like by using a mouse 1006 and a keyboard 1007. The respective constituent elements described above are communicatively connected to each other via a common bus 1008.

Figure 3:
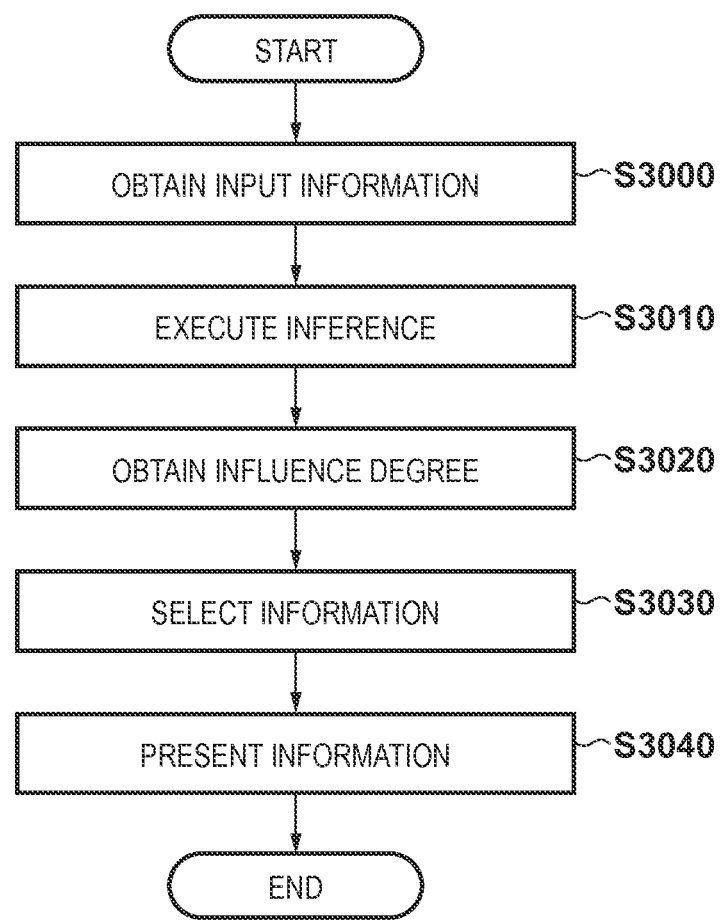
FIG. 3 is a flowchart showing a processing procedure in the first embodiment.

FIG. 3 is a flowchart showing a processing procedure in this embodiment. This embodiment is implemented by causing the CPU 1001 to execute a program for implementing the function of each unit, which is stored in the main memory 1002. In the following description, each image finding or clinical information name is represented by Ij (j=1 to m), and m types of image finding names or clinical information names I1 to Im are handled. In addition, k states which Ij can take are written as Sjk. The range of k varies in value depending on Ij. Assume that in this embodiment, it is possible to input or obtain image findings or clinical information like those shown in FIG. 4, and the respective image findings or clinical information can take states like those shown in FIG. 4. For example, "shape" of I1 represents the shape of an abnormal shadow, and takes three states, namely a state S11 "sphere", a state S12 "lobulated", and a state S13 "ragged". "Notch" of I2 represents the degree of notch in an abnormal shadow. In addition, "involvement (bronchus)" of I1 represents the presence/absence of the involvement of a bronchus in the abnormal shadow. Furthermore, "history of malignancy" of Im represents whether there is a history of malignancy of a disease in the past.

In the following description, a set of states Sjk is written as a set E. Assume, however, that a plurality of states Sjk corresponding to one Ij do not simultaneously exist in one set E. For example, if I1 takes states S11, S12, and S13, and I2 takes states S21, S22, S23, and S24, set E={S11, S21} holds, but set E={S11, S12} does not hold. This is because one image finding or clinical information takes only one state. In the following description, a diagnosis will be written as a symbol D. According to this embodiment, a diagnosis takes three values respectively that represent primary lung cancer (written as D1), lung cancer metastasis (written as D2), and others (written as D3). The inference probability of a diagnosis Dr (r=1, 2, 3) with input information being given as the set E will be written as P(Dr|E). Likewise, a subset of the set E is written as Ex, and the inference probability of the diagnosis Dr with the subset Ex being given is written as P(Dr|Ex). In addition, the influence degree of Ex with respect to the diagnosis Dr is written as I(Dr|Ex).

In step S3000, the input information obtaining unit 102 obtains input information and accompanying data concerning an abnormal shadow in a lung which is input to the decision support apparatus 100. Assume that the obtained input information includes I1 "shape": state S12 "lobulated", I2 "notch": state S21 "strong", . . . , I1 "involvement (bronchus)": state S11 "present", . . . , Im "history of malignancy": state Sm2 "none". In this case, the set E of the states $S_{jk}$ (that is, input information) is given as E={S12, S21, . . . , S11, . . . , Sm2}.

In step S3010, the inference unit 104 infers the probability (inference result) of the abnormal shadow being each diagnosis based on the input information (that is, E) obtained in step S3000. As an inference technique used at this time, it is possible to use various existing inference techniques such as a Bayesian network, neural network, and support vector machine. This embodiment uses the Bayesian network as an inference technique. The Bayesian network is an inference model using conditional probabilities. It is possible to obtain the inference probability of each diagnosis when input information is input (the probability of the case being each diagnosis; also called a posterior probability). In this embodiment, the probabilities of the diagnoses D1, D2, and D3 with respect to the abnormal shadow are obtained.

In step S3020, the influence degree obtaining unit 106 obtains an influence degree by using the input information obtained in step S3000 and the inference result obtained in step S3010. More specifically, the influence degree obtaining unit 106 obtains the subsets Ex (that is, subsets of input information) of at least one set E (that is, input information) and obtains an influence degree indicating the degree of influence of each subset Ex on each diagnosis. For example, in the above example of E={S12, S21, . . . , S11, . . . , Sm2}, when the subsets Ex with an element count of 2 are to be obtained, the subsets Ex such as {S12, S21}, {S12, S11}, and {S21, Sm2} are obtained. Assume that in this embodiment, all the subsets Ex with an element count of 1 are obtained. Therefore, in the above example, since E includes m elements, m subsets Ex are obtained.

Subsequently, the influence degree of each subset Ex is obtained. In this embodiment, an influence degree is calculated by using the prior probability of each diagnosis and an inference probability obtained when only Ex is input. Note that in this embodiment, the prior probability of each diagnosis corresponds to the probability of each diagnosis obtained when no information is input. For example, an influence degree I(Dr|Ex) of Ex with respect to the diagnosis Dr is calculated by $$I(D_r|E_x) = P(D_r|E_x) - P(D_r) \quad (1)$$

In equation (1), if I(Dr|Ex) is positive, that is, the posterior probability obtained when only Ex is input is higher than the prior probability, it is determined that Ex has an affirmative influence on Dr. In contrast, if I(Dr|Ex) is negative, that is, the posterior probability obtained when only Ex is input is lower than the prior probability, it is determined that Ex has a denial influence on Dr. Note that the above method of calculating influence degrees is an example of processing in this embodiment, and the embodiment is not limited to this.

In step S3030, the selection unit 108 selects a subset based on the inference results obtained in step S3010 and the influence degrees obtained in step S3020. In this embodiment, the selection unit 108 selects a subset in accordance with the inference probability of a diagnosis having the highest inference probability in the inference results and a threshold. More specifically, if the highest inference probability is equal to or more than a predetermined threshold, the selection unit 108 selects a subset affirming the diagnosis having the highest inference probability. In contrast, if the highest inference probability does not exceed the predetermined threshold, the selection unit 108 determines that the inference probability is low, and selects a subset denying diagnoses other than the diagnosis having the highest inference probability. Note that the above selection method is an example of processing in this embodiment, and the embodiment is not limited to this.

Processing to be performed in this embodiment when the threshold is 70.0% will be described in detail with reference to FIGS. 5A and 5B. FIGS. 5A and 5B respectively show the inference probabilities P(Dr|Ex) obtained by the processing in step S3010 and the influence degrees I(Dr|Ex) with respect to the respective diagnoses obtained by the processing in step S3020 when different pieces of input information (sets E) are obtained. Referring to FIG. 5A, the diagnosis having the highest inference probability is D1 (that is, primary lung cancer), and an inference probability P(D1|E) of the diagnosis is 47.6%. In this case, since the inference probability P(D1|E) does not exceed the threshold of 70.0%, the selection unit 108 selects information denying D2 and D3 other than D1, that is, subsets in which I(D2|Ex) and I(D3|Ex) exhibit negative values. In this embodiment, the selection unit 108 selects subsets, of the subsets Ex in which I(D2|Ex) and I(D3|Ex) exhibit negative values, which take the minimum values. More specifically, in the embodiment, the selection unit 108 selects {Sm2} (=−13.8%) and {S43} (=−8.80).

On the other hand, referring to FIG. 5B, the diagnosis having the highest inference probability is D2 (that is, lung cancer metastasis), and an inference probability P(D2|E) of the diagnosis is 82.1%. In this case, since the inference probability P(D2|E) exceeds the threshold of 70.0%, the selection unit 108 selects information affirming D2, that is, subsets in which I(D2|Ex) exhibits positive values. In this embodiment, the selection unit 108 selects a subset, of the subsets Ex in which I(D2|Ex) exhibits positive values, which takes the maximum value. More specifically, in this embodiment, the selection unit 108 selects {S11} (=10.4).

In step S3040, the presentation unit 110 generates and displays information to be presented. More specifically, the presentation unit 110 generates information to be presented based on the input information and accompanying data obtained in step S3000, the inference result obtained in step S3010, and the information of the subset selected in step S3030. FIG. 6 shows an example of presentation information to be displayed on the monitor 1005 in this embodiment when the inference result and the influence degree shown in FIG. 5A are obtained. Presentation information 600 includes a representative image 6000 of an abnormal shadow in a lung obtained in step S3000 and input information 6010 of the abnormal shadow in the lung. The presentation information 600 includes an inference result 6020 inferred in step S3010. In the case shown in FIG. 6, as the inference result 6020, an inference probability 6021 of primary lung cancer, an inference probability 6022 of lung cancer metastasis, and an inference probability 6023 of others in the inference result are displayed in a pie chart. In addition, the presentation information 600 includes a diagnosis (primary lung cancer in the case shown in FIG. 6), of the respective diagnoses in the inference result, from which the highest inference probability is obtained, and a probability 6030 (the inference probability of primary lung cancer in the case shown in FIG. 6). In addition, the presentation information 600 includes supporting information 6040 selected by the processing in step S6030.

According to this embodiment, the method of selecting supporting information is changed in consideration of the inference probability of an inference result. More specifically, if the inference probability of a diagnosis as a target is high, information affirming the diagnosis is selected. If the inference probability is low, information denying other diagnoses is selected. This makes it possible to present, as supporting information, information like that obtained when the doctor performs radiogram interpretation. This makes it possible to efficiently present information necessary for the doctor. In other words, according to this embodiment, since information is selected and presented in accordance with the confidence degree of a diagnosis as a target, it is possible to efficiently present information necessary for the user.

[First Modification]

In the first embodiment, in step S3030, information is selected in accordance with the inference probability of a diagnosis having the highest inference probability and a threshold. However, it is possible to use not only the highest inference probability of a diagnosis but also the inference probability of another diagnosis as criteria for selection. For example, information may be selected in accordance with whether the difference/ratio between the inference probability of a diagnosis having the highest inference probability and the inference probability of a diagnosis having the second highest inference probability exceeds a predetermined threshold. Alternatively, it is possible to use the difference/ratio between the inference probability of a diagnosis having the highest inference probability and the inference probability of a diagnosis having the lowest inference probability and a threshold. In addition, it is possible to use the difference/ratio between the inference probability of a diagnosis having the highest inference probability and the total sum of second to Nth highest inference probabilities or the difference/ratio between the inference probability of a diagnosis having the highest inference probability and the median value of the inference probabilities of the respective diagnoses. This makes it possible to dynamically select information and hence to flexibly present information necessary for the doctor.

[Second Modification]

In the first embodiment, information is selected in accordance with the inference probability of a diagnosis having the highest inference probability and a threshold in step S3030. However, the inference probability of a diagnosis having the second or subsequent highest inference probability may be used as a criterion for selection. For example, it is possible to select information by using the inference probability of a diagnosis having the lowest inference probability and a threshold.

[Third Modification]

In the first embodiment, information is selected by using the inference probability of a diagnosis having the highest inference probability in step S3030. However, it is possible to use the inference probability of a diagnosis identified by another method instead of a diagnosis having the highest inference probability. For example, information may be selected in accordance with the inference probability of a diagnosis designated by a doctor. According to this technique, information is selected in accordance with the diagnosis desired by the doctor, and hence it is possible to efficiently present information necessary for the doctor.

[Fourth Modification]

In step S3030, when selecting information denying diagnoses other than a target diagnosis, information is selected by simultaneously using the influence degree of each diagnosis other than the target diagnosis. However, information may be selected by using the influence degree of a diagnosis as a target. More specifically, it is possible to select information affirming a target diagnosis and denying other diagnoses. In addition, it is possible to select information simultaneously denying a plurality of diagnoses other than a target diagnosis. With this technique, information is selected by using the influence degrees of a plurality of diagnoses. This makes it possible to efficiently present information more necessary for a doctor.

[Fifth Modification]

In step S3030, if the inference probability of a diagnosis having the highest inference probability exceeds a threshold, information affirming the diagnosis is presented, whereas if the inference probability does not exceed the threshold, information denying other diagnoses is presented. However, other methods may be used. More specifically, if the inference probability of a diagnosis exceeds the threshold, information denying other diagnoses is presented, whereas if the inference probability does not exceed the threshold, information affirming the diagnosis may be presented.

According to this method, since information is presented from a viewpoint opposite to a method generally employed by a doctor, information can be expected to be used to call attention when the doctor performs diagnosis.

As has been described above, according to these embodiments, it is possible to provide proper supporting information based on the inference probability of each diagnosis which is obtained from the image findings and clinical information contained in medical information and the influence degrees of subsets including findings and clinical information with respect to inferences associated with the inference probabilities.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-144857, filed Jul. 10, 2013 which is hereby incorporated by reference herein in its entirety.

What is claimed is:

1. A diagnosis support system comprising:
one or more processors; and
one or more memories coupled to the one or more processors and having stored thereon instructions which, when executed by the one or more processors, cause the diagnosis support system to:
obtain input information corresponding to a case;
identify a diagnosis corresponding to the case based on the input information and obtain an inference probability of the diagnosis;
select at least one of affirmative information or denial information as supporting information for the identified diagnosis based on the inference probability of the identified diagnosis; and
display the supporting information of the identified diagnosis on a display unit,
wherein the affirmative information has an affirmative influence on the inference probability of the identified diagnosis, and
wherein the denial information has a denial influence on the inference probability of diagnoses other than the identified diagnosis.

2. The system according to claim 1, wherein the instructions, when executed by the one or more processors, further cause the diagnosis support system to obtain an influence degree of the input information with respect to the identified diagnosis, and
wherein at least one of the affirmative information or the denial information is selected as the supporting information based on the influence degree.

3. The system according to claim 2, wherein the affirmative information having the influence degree which affirms the identified diagnosis is selected in a case where an inference probability of the identified diagnosis is higher than a predetermined criterion.

4. The system according to claim 2, wherein the denial information having an influence degree which denies diagnoses other than the identified diagnosis is selected in a case where the inference probability of the identified diagnosis is lower than a predetermined criterion.

5. The system according to claim 2, wherein the affirmative information having an influence degree which affirms the identified diagnosis and the denial information having an influence degree which denies diagnoses other than the identified diagnosis is selected in a case where the inference probability of the identified diagnosis is lower than a predetermined criterion.

6. The system according to claim 1, wherein the identified diagnosis is a diagnosis having a highest inference probability with respect to the diagnosis.

7. The system according to claim 1, wherein the identified diagnosis is identified by user designation.

8. A method of controlling a diagnosis support system, the method comprising:
input information corresponding to a case;
identifying a diagnosis corresponding to the case based on the input information and obtaining an inference probability of the diagnosis;
selecting at least one of affirmative information or denial information as supporting information for the identified diagnosis based on the inference probability of the identified diagnosis; and
displaying the supporting information of the identified diagnosis on a display unit,
wherein the affirmative information has an affirmative influence on the inference probability of the identified diagnosis, and
wherein the denial information has a denial influence on the inference probability of diagnoses other than the identified diagnosis.

9. A non-transitory computer-readable storage medium storing a program for causing a computer to execute each step of a decision support method, the decision support method comprising:
obtaining input information corresponding to a case;
identifying a diagnosis corresponding to the case based on the input information and obtaining an inference probability of the diagnosis;
selecting at least one of affirmative information or denial information as supporting information for the identified diagnosis based on the inference probability of the identified diagnosis; and
displaying the supporting information of the identified diagnosis on a display unit,
wherein the affirmative information has an affirmative influence on the inference probability of the identified diagnosis, and
wherein the denial information has a denial influence on the inference probability of diagnoses other than the identified diagnosis.

10. The system according to claim 1, wherein at least the denial information is selected as the supporting information of the identified diagnosis in a case where the inference probability of the identified diagnosis is lower than a predetermined criterion.

11. The system according to claim 1, wherein at least the affirmative information is selected as the supporting information of the identified diagnosis in a case where the inference probability of the identified diagnosis is higher than a predetermined criterion.

12. The system according to claim 1, wherein at least the affirmative information is selected as the supporting information of the identified diagnosis in a case where the inference probability of the identified diagnosis is higher than a predetermined criterion, and at least the denial information is selected as the supporting information of the identified diagnosis in a case where the inference probability of the identified diagnosis is lower than the predetermined criterion.

13. The system according to claim 1, wherein the affirmative information and the denial information is selected as the supporting information of the identified diagnosis in a case where the inference probability of the identified diagnosis is lower than a predetermined criterion.

14. A diagnosis support system for performing inference about diagnosis names, the system comprising:
one or more processors; and
one or more memories coupled to the one or more processors and having stored thereon instructions which, when executed by the one or more processors, cause the diagnosis support system to:
obtain input information about findings;
calculate an inference probability of the diagnosis names based on the input information; and
display denial information on a display unit in a case where a calculated probability of a target diagnosis name of the diagnosis names is lower than a predetermined criterion, wherein the denial information is related to the input information in which the probability of at least one of the diagnosis names other than the target diagnosis name is reduced.

15. The system according to claim 14, wherein affirmative information is displayed on a display unit in a case where the probability of the target diagnosis name is higher than the predetermined criterion, and wherein the affirmative information is related to the input information in which the probability of the target diagnosis name is increased.

16. The system according to claim 14, wherein the target diagnosis name is a diagnosis name having a highest probability.

17. The system according to claim 14, wherein the target diagnosis name is identified by user designation.

18. The system according to claim 14, wherein the instructions, when executed by the one or more processors, further cause the diagnosis support system to display a chart showing the inference probability of the diagnosis names.

19. A method of controlling a diagnosis support system for performing inference about diagnosis names, the method comprising:

obtaining input information about findings;

calculating an inference probability of the diagnosis names based on the input information; and displaying denial information on a display unit in a case where a calculated probability of a target diagnosis name included in the diagnosis names is lower than a predetermined criterion, wherein the denial information is related to the input information in which the probability of at least one of the diagnosis names other than the target diagnosis name is reduced.

20. The method according to claim 19, wherein the displaying includes displaying affirmative information on a display unit in a case where the probability of the target diagnosis name is higher than the predetermined criterion, and wherein the affirmative information is the input information in which the probability of the target diagnosis name is increased.

* * * * *